United States Patent [19]

Furmanek et al.

[11] Patent Number: 5,955,637

[45] Date of Patent: Sep. 21, 1999

[54] PRODUCTION OF DIHALOMETHANES CONTAINING FLUORINE AND AZEOTROPES OF DIHALOMETHANES CONTAINING CHLORINE WITH HF

[75] Inventors: Paul S. Furmanek, Newark; David A. Glasscock, Bear; Michael Keane, Jr., Wilmington, all of Del.

[73] Assignee: E. I. du Pont de Nemours and Company, Wilmington, Del.

[21] Appl. No.: 08/458,604

[22] Filed: Jun. 2, 1995

Related U.S. Application Data

[62] Division of application No. 08/146,334, Nov. 1, 1993.

[51] Int. Cl.⁶ .............................. C07C 19/08; C07C 21/00
[52] U.S. Cl. .............................................. 570/134; 570/181
[58] Field of Search ................................... 570/175, 134, 570/181

[56] References Cited

U.S. PATENT DOCUMENTS

| | | |
|---|---|---|
| 2,110,369 | 3/1938 | Leicester . |
| 2,946,827 | 7/1960 | Belf . |
| 3,632,834 | 1/1972 | Christoph . |
| 4,147,733 | 4/1979 | Fiske et al. . |
| 4,944,846 | 7/1990 | Manzer et al. . |
| 5,136,113 | 8/1992 | Rao . |
| 5,208,395 | 5/1993 | Eisheikh . |
| 5,523,015 | 6/1996 | Tsuda et al. . |

FOREIGN PATENT DOCUMENTS

| | | |
|---|---|---|
| 0 128 510 | 12/1984 | European Pat. Off. . |
| 0 403 108 | 12/1990 | European Pat. Off. . |
| 0 508 660 | 10/1992 | European Pat. Off. . |
| 59-225131 | 12/1984 | Japan . |
| 896068 | 5/1962 | United Kingdom . |
| WO 93/21140 | 10/1993 | WIPO . |

OTHER PUBLICATIONS

Smisek, M. et al, *Active Carbon*, pp. 61–70, 1970.
Hassler, J. W., *Activated Carbon*, pp. 344–345, 1963.
Gervasutti. C, et al. *J. Fluorine Chem.*, 19, pp. 1–20, 1981/82.
Schotte, W., *Ind. Eng. Chem. Process Des. Dev.*, 19, pp. 432–439, 1980.
Marangoni, L. et al, "Catalyst for fluorination of organic chlorocompounds", *LaChimica E L'Industria*, 64(3), 135–140 (1982).
Horsley, L.H., Editor, "Azeotropic Data—III", *Advances in Chemistry Series 116, American Chemical society*, Washington, DC (1973).
Patent Abstracts of Japan, 9(91) re JP 59–225131 (1985).
Patent Abstracts of Japan, 9(125), re JP 60–013726 (1985).

*Primary Examiner*—Alan Siegel

[57] ABSTRACT

A process for producing difluoromethane is disclosed which includes the step of contacting a gaseous mixture containing $CH_2Cl_2$ and hydrogen fluoride with a catalyst containing a catalytically effective amount of trivalent chromium supported on a carbon having an ash content of less than 0.5 percent by weight, at a temperature of from about 180° C. to about 375° C. The catalyst and temperature conditions of this process allow the concurrent reaction $CCl_3CF_3$ with HF to form $CCl_2FCF_3$. $CH_2ClF$ and unreacted $CH_2Cl_2$, each of which may be recovered as an azeotrope with HF, may be recycled.

11 Claims, No Drawings

PRODUCTION OF DIHALOMETHANES CONTAINING FLUORINE AND AZEOTROPES OF DIHALOMETHANES CONTAINING CHLORINE WITH HF

This a division of application Ser. No. 08/146,334, filed Nov. 1, 1993.

FIELD OF THE INVENTION

This invention relates to the production of halocarbons and their azeotropes and more particularly to the production of difluoromethane (i.e., $CH_2F_2$ or HFC-32) and azeotropes of chlorine-containing precursors thereof (i.e., $CH_2ClF$ or HCFC-31, and $CH_2Cl_2$) with HF.

BACKGROUND

Chlorofluorocarbons (i.e., CFCs) are compounds containing only carbon, fluorine and chlorine. Various CFCs have been used for many years as refrigerants, heat transfer media, foam expansion agents, aerosol propellants, solvents and power cycle working fluids. However, there has been recent concern that CFCs may be detrimental to the Earth's ozone layer. Consequently, there is a worldwide effort to find alternative compounds which contain fewer or preferably no chlorine substituents. The hydrofluorocarbon difluoromethane has been proposed as a replacement for some CFCs, particularly, in refrigeration, air-conditioning and other applications (see e.g., European Patent Application Publication No. 508,660 A1). Accordingly, there is interest in developing efficient processes for the production of HFC-32.

Japanese Patent Publication 59-225131 discloses preparation of HFC-32 by reacting dichloromethane with HF in the vapor phase at 200 to 500° C. in the presence of a catalyst which consists of chromium fluoride or which has been obtained by molding a mixture of chromium fluoride and a carrier or by supporting chromium fluoride on a carrier. Chromium fluoride may be obtained by fluorinating a chromium-containing compound. Immersion of activated carbon in a solution of chromium chloride, followed by treatment with HF is disclosed (see e.g., Example 2). It is well known that activated carbon typically has an ash content comprising metal-containing compounds (e.g., potassium and sodium oxides) and other impurities (see e.g., M. Smisek et al. "Active Carbon", pages 61–70 (1970) and J. W. Hassler "Activated Carbon", pages 344–345 (1963)).

1,1-Dichlorotetrafluoroethane (i.e., $CCl_2FCF_3$ or CFC-114a) is of interest as an intermediate for producing 1,1,1,2-tetrafluoroethane (i.e., $CF_3CH_2F$ or HFC-134a). $CF_3CH_2F$ can be obtained by the catalytic hydrogenolysis of $CCl_2FCF_3$ using a supported metal hydrogenation catalyst (see e.g., C. Gervasutti et al., J. Fluorine Chem., 1981/82, 19, pgs. 1–20). The HFC-134a is an environmentally acceptable potential replacement for CFC refrigerants, blowing agents, aerosol propellants and sterilants that are implicated in the destruction of stratospheric ozone.

SUMMARY OF THE INVENTION

The present invention provides a process for producing difluoromethane. The process comprises the step of contacting a gaseous mixture containing $CH_2Cl_2$ and hydrogen fluoride with a catalyst containing a catalytically effective amount of trivalent chromium supported on a carbon having an ash content of less than 0.5 percent by weight, at a temperature of from about 180° C. to about 375° C. The catalyst and temperature conditions of this process allow the concurrent reaction of 1,1,1-trichlorotrifluoroethane (i.e., $CCl_3CF_3$ or CFC-113a) with HF to form CFC-114a. $CH_2ClF$ and unreacted $CH_2Cl_2$, each of which may be recovered as an azeotrope with HF, may be recycled.

The present invention also provides compositions which consist essentially of hydrogen fluoride in combination with an effective amount of a compound selected from the group consisting of $CH_2Cl_2$ and $CH_2ClF$ to form an azeotrope or azeotrope-like composition with hydrogen fluoride, said composition containing from about 5 to 29 mole % $CH_2Cl_2$ or from about 58 to 65 mole % $CH_2ClF$.

DETAILED DESCRIPTION

The present invention provides a process for the vapor-phase catalytic fluorination of $CH_2Cl_2$ to $CH_2F_2$. The process may be used for the vapor-phase catalytic fluorination of mixtures of $CH_2Cl_2$ and $CCl_3CF_3$ to produce both $CH_2F_2$ and $CCl_2FCF_3$. The process of this invention employs catalyst compositions comprising trivalent chromium. In addition to a catalytically effective amount of trivalent chromium such fluorination catalysts can include other components to increase catalyst activity and/or life such as one or more divalent metal cations (e.g., zinc, magnesium and/or cobalt). While unsupported trivalent chromium catalysts (e.g., $Cr_2O_3$) or trivalent chromium catalysts supported on non-carbon supports (e.g., on alumina, aluminum fluoride, or magnesium fluoride) may also catalyze the reaction of $CH_2Cl_2$ to $CH_2F_2$, this invention advantageously involves trivalent chromium (e.g., $CrCl_3$ and/or $CrF_3$) supported on a carbon which has an ash content of less than 0.5 weight percent. A $CrF_3$ on carbon is disclosed in U.S. Pat. No. 3,632,834, the contents of which are incorporated herein by reference. Catalysts suitable for use in the process of this invention can be prepared in a manner similar to that disclosed in U.S. Pat. No. 3,632,834, provided the carbon used has an ash content of less than 0.5 weight percent. Preferred catalysts include a low ash content carbon support (as described herein) containing chromium chloride ($CrCl_3$), fluorided chromium chloride (e.g., $CrCl_3$ treated with HF to produce chromium chlorofluoride(s)), or mixtures of chromium chloride and chromium fluoride ($CrF_3$). While such low-ash carbon supports may be obtained using a variety of methods, a preferred carbon support is acid-washing activated carbon prior to impregnating it with trivalent chromium. Preferably the chromium content (expressed as $CrCl_3$) is from about 5 to 60 weight percent of the carbon supported catalyst.

The initial acid treatment typically uses an acid other than hydrofluoric acid. Preferred acids used for the acid treatment contain neither phosphorus nor sulfur. Examples of acids which may be used in the initial acid wash during the catalyst preparation process include organic acids such as acetic acid and inorganic acids such as hydrochloric acid or nitric acid. Preferably, hydrochloric acid or nitric acid is used. The second acid treatment, when employed, advantageously uses hydrofluoric acid. Preferably, the carbon is treated with acid such that after such treatment the carbon contains less than about 0.2% by weight ash.

Commercially available carbons which may be treated with acids to provide suitable supports include those sold under the following trademarks: Darco™, Nuchar™, Columbia SBV™, Columbia MBV™, Columbia MBQ™, Columbia JXC™, Columbia CXC™, Calgon PCB™, Norit™ and Barnaby Cheny NB™. The carbon support can be in the form of powder, granules, or pellets, etc.

The acid treatment may be accomplished in several ways. A suitable procedure is as follows. A carbon support is soaked overnight with gentle stirring in a 1 molar solution of the acid prepared in deionized water. The carbon support is then separated and washed with deionized water until the pH of the washings is about 3. Preferably, the carbon support is then soaked again with gentle stirring in a 1 molar solution of the acid prepared in deionized water for 12 to 24 hours. The carbon support is then finally washed with deionized water until the washings are substantially free of the anion of the acid (e.g., Cl$^-$ or NO$_3^-$), when tested by standard procedures. The carbon support is then separated and dried at about 120° C. The washed carbon is then soaked, if necessary, in 1 molar HF prepared in deionized water for about 48 hours at room temperature with occasional stirring. The carbon support is separated and washed repeatedly with deionized water until the pH of the washings is greater than 4. The carbon support is then dried followed by calcination at 300° C. for about 3 hours in air prior to its use as a support. Reference is made to U.S. Pat. No. 5,136,113 for further details relating to producing acid-washed carbon catalysts.

Typically, where the starting material to be fluorinated consists essentially of CH$_2$Cl$_2$, the molar ratio of HF added to CH$_2$Cl$_2$ starting material added (whether or not CH$_2$ClF, unreacted CH$_2$Cl$_2$ and/or HF are also recycled) ranges from about 0.5:1 to about 10:1, and is preferably from about 1:1 to 8:1, more preferably about 2:1 to 6:1. Typically, where the starting material to be fluorinated consists essentially of a mixture of CH$_2$Cl$_2$ and CCl$_3$CF$_3$, the molar ratio of HF added to the total amount of CH$_2$Cl$_2$ and CCl$_3$CF$_3$ starting material added typically ranges from about 0.5:1 to about 10:1, and is preferably from about 1:1 to 8:1. Typically, the molar ratio of CH$_2$Cl$_2$ to CCl$_3$CF$_3$ in mixtures ranges from about 1:9 to about 9:1.

Suitable reaction temperatures range from about 180° C. to about 375° C. Preferably, the reaction temperature is in the range of from about 200° C. to about 350° C. Pressure is not critical. Atmospheric and superatmospheric pressures (e.g., from about 100 kPa to about 7000 kPa) are the most convenient and are therefore preferred.

The fluorination reaction is performed in the vapor phase using well known chemical engineering practice, which includes continuous, semi-continuous or batch operations. The fluorination reaction may be done in the presence of inert gases e.g., nitrogen, helium or argon.

The reaction product stream can be treated in accordance with any of the techniques known to the art for separating the desired fluorination product from by-product hydrogen chloride, unreacted hydrogen fluoride, chlorofluoromethane and other minor by-products. For example, HFC-32 can be separated from the other components of the reaction products by distillation. It has been found that during this distillation that chlorofluoromethane (i.e., CH$_2$ClF or HCFC-31) can form a binary azeotrope with HF. It has also been found that CH$_2$Cl$_2$ can form a binary azeotrope with HF. Accordingly, the CH$_2$ClF and unreacted CH$_2$Cl$_2$ can each be recovered as a composition consisting essentially of an azeotrope thereof and HF, using distillation. Further discussion of these azeotropes is provided below.

Alternatively, the product stream may be scrubbed with water or aqueous alkali to remove hydrogen halides, dried with a drying agent, such as silica gel or a molecular sieve adapted to such purpose and recovered. Preferably, CH$_2$ClF and unreacted CH$_2$Cl$_2$ and/or their azeotropes with hydrogen fluoride are recycled to the fluorination reactor.

The reactors, separators and their associated feed lines, effluent line and associated units should be constructed of materials resistant to hydrogen fluoride, hydrogen chloride and chlorine. Typical materials of construction, well-known to the fluorination art, include stainless steels, in particular of the austentic type, and the well-known high nickel alloys, such as Monel® nickel-copper alloys, Hastelloy® nickel-based alloys and, Inconel® nickel-chromium alloys. Also suitable for reactor fabrication are such polymeric plastics as polytrifluorochloroethylene and polytetrafluoroethylene, generally used as linings.

As noted above, the present invention provides a composition which consists essentially of hydrogen fluoride and an effective amount of a compound selected from the group consisting of CH$_2$Cl$_2$ and CH$_2$ClF to form an azeotropic composition with hydrogen fluoride. By effective amount is meant an amount which, when combined with HF, results in the formation of an azeotrope or azeotrope-like mixture. As recognized in the art, an azeotrope or an azeotrope-like composition is an admixture of two or more different components which, when in liquid form under given pressure, will boil at a substantially constant temperature, which temperature may be higher or lower than the boiling temperatures of the components, and which will provide a vapor composition essentially identical to the liquid composition undergoing boiling.

For the purpose of this discussion, azeotrope-like composition means a composition that behaves like an azeotrope (i.e., has constant-boiling characteristics or a tendency not to fractionate upon boiling or evaporation). Thus the composition of the vapor formed during boiling or evaporation is the same as or substantially the same as the original liquid composition. Hence, during boiling or evaporation, the liquid composition, if it changes at all, changes only to a minimal or negligible extent. This is to be contrasted with non-azeotrope-like compositions in which during boiling or evaporation, the liquid composition changes to a substantial degree.

Accordingly, the essential features of an azeotrope or an azeotrope-like composition are that at a given pressure, the boiling point of the liquid composition is fixed and that the composition of the vapor above the boiling composition is essentially that of the boiling liquid composition (i.e.., no fractionation of the components of the liquid composition takes place). It is also recognized in the art that both the boiling point and the weight percentages of each component of the azeotropic composition may change when the azeotrope or azeotrope-like liquid composition is subjected to boiling at different pressures. Thus an azeotrope or an azeotrope-like composition may be defined in terms of the unique relationship that exists among components or in terms of the compositional ranges of the components or in terms of exact weight percentages of each component of the composition characterized by a fixed boiling point at a specified pressure. It is also recognized in the art that various azeotropic compositions (including their boiling points at particular pressures) may be calculated (see, e.g., W. Schotte Ind. Eng. Chem. Process Des. Dev. 1980, 19, pp. 432–439). Experimental identification of azeotropic compositions involving the same components may be used to confirm the accuracy of such calculations and/or to modify the calculations at the same or other temperatures and pressures.

Compositions may be formed which consist essentially of azeotropic combinations of hydrogen fluoride with a compound selected from the group consisting of CH$_2$Cl$_2$ and CH$_2$ClF. These include a composition consisting essentially of from about 42 to about 35 mole percent HF and from about 58 to about 65 mole percent CH$_2$ClF (which form an azeotrope boiling at a temperature from about −25° C. to about 75° C. and a pressure between about 55 kPa and about 1700 kPa); and a composition consisting essentially of from about 95 to about 71 mole percent HF and from about 5 to about 29 mole percent $CH_2Cl_2$ (which form an azeotrope boiling at a temperature from about −50° C. to about 110° C. and a pressure between about 5 kPa and about 2280 kPa).

To determine the relative volatility of HF with $CH_2Cl_2$ and with $CH_2ClF$, the so-called PTx Method was used. In this procedure, the total absolute pressure in a cell of known volume is measured at a constant temperature for various known binary compositions. Use of the PTx Method is described in greater detail in "Phase Equilibrium in Process Design", Wiley-Interscience Publisher, 1970, written by Harold R. Null, on pages 124 to 126, the entire disclosure of which is hereby incorporated by reference. Samples of the vapor and liquid were obtained and analyzed to verify their respective compositions.

These measurements can be reduced to equilibrium vapor and liquid compositions in the cell by an activity coefficient equation model, such as the Non-Random, Two-Liquid (NRTL) equation, to represent liquid phase non-idealities. Use of an activity coefficient equation, such as the NRTL equation, is described in greater detail in "The Properties of Gases and Liquids", 4th Edition, publisher McGraw Hill, written by Reid, Prausnitz and Poling, on pages 241 to 387; and in "Phase Equilibria in Chemical Engineering", published by Butterworth Publishers, 1985, written by Stanley M. Walas, pages 165 to 244; the entire disclosure of each of the previously identified references are hereby incorporated by reference.

Without wishing to be bound by any theory or explanation, it is believed that the NRTL equation can sufficiently predict whether or not mixtures of HF and either $CH_2Cl_2$ or $CH_2ClF$ behave in an ideal manner, and can sufficiently predict the relative volatilities of the components in such mixtures. Where the relative volatility approaches 1.0 defines the system as forming a near-azeotrope. Where the relative volatility is 1.0 defines the system as forming an azeotrope.

It has been found that azeotropes of HCFC-31 and HF are formed at a variety of temperatures and pressures. Between 55 kPa (at a temperature of −25° C.) and 1700 kPa (at a temperature of 75° C.) azeotropic compositions consisting essentially of HCFC-31 and HF range from about 42 mole percent HF (and 58 mole percent HCFC-31) to about 35 mole percent HF (and 65 mole percent HCFC-31). An azeotrope of HF and $CH_2ClF$ has been found at 20° C. and 49.3 psia (340 kPa) consisting essentially of 37.5 mole percent HF and 62.5 mole percent $CH_2ClF$. Based upon the above findings, it has been calculated that an azeotropic composition of about 4.2 mole percent HF and 58 mole percent HCFC-31 can be formed at −25° C. and 55 kPa and an azeotropic composition of about 35 mole percent HF and 65 mole percent HCFC-31 can be formed at 75° C. and 1700 kPa. Accordingly, the present invention provides an azeotrope or azeotrope-like composition consisting essentially of from about 42 to about 35 mole percent HF and from about 58 to 65 mole percent $CH_2ClF$, said composition having a boiling point from about −25° C. at 55 kPa to about 75° C. at 1700 kPa.

It has been found that azeotropes of $CH_2Cl_2$ and HF are formed at a variety of temperatures and pressures. Between 5 kPa (at a temperature of −50° C.) and 2280 kPa (at a temperature of 110° C.) azeotropic compositions consisting essentially of $CH_2Cl_2$ and HF range from about 95 mole percent HF (and 5 mole percent $CH_2Cl_2$) to about 71 mole percent HF (and 29 mole percent $CH_2Cl_2$). An azeotrope of HF and $CH_2Cl_2$ has been found at 20° C. and 20.8 psia (143 kPa) consisting essentially of 85 mole percent HF and 15 mole percent $CH_2Cl_2$. Based upon the above findings, it has been calculated that an azeotropic composition of about 95 mole percent HF and 5 mole percent $CH_2Cl_2$ can be formed at −50° C. and 5 kPa and an azeotropic composition of about 71 mole percent HF and 29 mole percent $CH_2Cl_2$ can be formed at 110° C. and 2280 kPa. Accordingly, the present invention provides an azeotrope or azeotrope-like composition consisting essentially of from about 95 to about 71 mole percent HF and from about 5 to 29 mole percent $CH_2Cl_2$, said composition having a boiling point from about −50° C. at 5 kPa to about 110° C. at 2280 kPa. These azeotropes are considered to be heterogeneous in that two liquid phases are present.

It will be apparent to one of ordinary skill in the art that distillation including azeotropes with HF can typically be run under more convenient conditions than distillation without HF (e.g., where HF is removed prior to distillation).

Practice of the invention will become further apparent from the following non-limiting examples.

EXAMPLES

Activation Procedure

A 5/8 41 (1.58 cm) I.D. Inconel® nickel alloy reactor was charged with a catalyst and heated to 300° C. in a flow of nitrogen (25 mL/min) for about 20 hours. The temperature was reduced to 175° C. and a 2:1 molar ratio of nitrogen and HF was started through the reactor (total flow 100 mL/min). After one hour under these conditions, the molar ratio of nitrogen to HF was adjusted to 1:3 and the temperature increased gradually over a two hour period to 400° C. The reactor was then brought back to the desired operating temperature, the nitrogen flow stopped, and the flow of reactants started.

Analytical Procedure

The reactor effluent was sampled on-line at various run times (R.T.s) with a Hewlett Packard HP 5890 gas chromatograph using a 20 foot (6.1 m) long, one-eighth inch (0.32 cm) diameter, column containing Krytox™ perfluorinated polyether on an inert support and a helium flow of 35 mL/min. Gas chromatographic conditions were 70° C. for three minutes followed by temperature programming to 180° C. at a rate of 6° C./minute. The table percentages are in area % unless noted otherwise.

Carbons Used

The examples used either Carbon A, a 6×16 mesh (about 3.4 mm×1.2 mm) commercial grade coconut shell carbon which had (before washing) an ash content of about 2.3 weight percent; or Carbon B, a 4×8 mesh (about 4.7 mm×2.4 mm) commercial grade coconut shell carbon which had (before washing) an ash content of about 2.6 weight percent. After water washing, Carbon A had an ash content of about 1 weight percent, and after HCl acid washing, Carbon A had an ash content of about 0.2 weight percent. After HCl acid washing, Carbon B had an ash content of less than about 0.1 weight percent.

Example 1

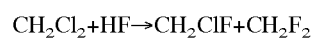

The reactor was charged with a 6% $CrCl_3$ on HCl-washed coconut Carbon A (30 mL, 14.7 g) catalyst and the catalyst was activated according to the Activation Procedure above. The reaction temperature was varied from 200 to 275° C., the molar ratio of HF to $CH_2Cl_2$ was varied from 2:1 to 6:1 and the contact time was 30 seconds in all cases. The reaction effluent was analyzed according to the Analytical Procedure above. The reaction results are shown in Table 1.

TABLE 1

| Run Time (Hours) | Temp. °C. | Molar Ratio HF:CH$_2$Cl$_2$ | %32 | %31 | %30 |
|---|---|---|---|---|---|
| 1 | 275 | 4:1 | 49.1 | 13.5 | 37.4 |
| 5 | 250 | 4:1 | 45.9 | 12.6 | 41.5 |
| 21 | 225 | 4:1 | 45.2 | 11.7 | 43.1 |
| 24.5 | 200 | 4:1 | 15.2 | 12.9 | 72.0 |
| 31 | 250 | 6:1 | 55.8 | 12.2 | 32.0 |
| 35.5 | 250 | 2:1 | 26.4 | 11.8 | 61.8 |

32 is CH$_2$F$_2$
31 is CH$_2$ClF
30 is CH$_2$Cl$_2$

Example 2

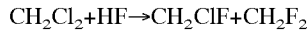
$CH_2Cl_2 + HF \rightarrow CH_2ClF + CH_2F_2$

The reactor was charged with a 7.5% CrCl$_3$ on HCl-washed Carbon B (15 mL, 6.22 g) catalyst and the catalyst was activated according to the Activation Procedure above. The reaction temperature was varied from 200 to 275° C., the molar ratio of HF to halocarbon feed was varied from 2:1 to 6:1 and the contact time (C.T.) was varied from 2 to 30 seconds. The halocarbon feed consisted of 98.7 mole percent CH$_2$Cl$_2$ and 1.3 mole percent CH$_2$ClF. The reaction effluent was analyzed according to the Analytical Procedure above. The reaction results, in mole percent, are shown in Table 2.

TABLE 2

| Run Time (Hours) | Temp. °C. | Molar Ratio HF:CH$_2$Cl$_2$ | C.T. Seconds | %32 | %31 | %30 |
|---|---|---|---|---|---|---|
| 13.0 | 200 | 2:1 | 15 | 2.2 | 7.6 | 90.2 |
| 23.5 | 225 | 2:1 | 15 | 33.3 | 12.0 | 54.6 |
| 37.0 | 225 | 4:1 | 15 | 50.1 | 12.1 | 37.7 |
| 45.0 | 250 | 4:1 | 15 | 53.5 | 13.0 | 33.5 |
| 60.0 | 250 | 2:1 | 15 | 34.0 | 13.1 | 53.0 |
| 68.5 | 275 | 2:1 | 15 | 34.3 | 14.1 | 51.6 |
| 72.5 | 275 | 4:1 | 15 | 60.8 | 13.4 | 25.9 |
| 88.0 | 275 | 4:1 | 30 | 59.7 | 13.4 | 26.8 |
| 92.0 | 275 | 4:1 | 5 | 52.6 | 14.0 | 33.4 |
| 94.0 | 275 | 6:1 | 5 | 65.8 | 12.6 | 21.7 |
| 95.5 | 275 | 6:1 | 2 | 55.2 | 13.2 | 31.7 |

Comparative Example A

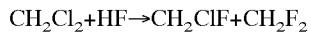
$CH_2Cl_2 + HF \rightarrow CH_2ClF + CH_2F_2$

The reactor was charged with a 7.5% CrCl$_3$ on Carbon A (15 mL, 6.4 g) catalyst, which was not acid-washed. The catalyst was then activated according to the Activation Procedure above. The reaction temperature was varied from 200 to 275° C., the molar ratio of HF to CH$_2$Cl$_2$ was varied from 2:1 to 4:1 and the contact time was 15 seconds in all cases. The CH$_2$Cl$_2$ feed to the reactor contained 98.9% CH$_2$Cl$_2$ and 1.1% CH$_2$ClF. The reaction effluent was analyzed according to the Analytical Procedure above. The reaction results are shown in Table A. Comparison of the results in Table A with results using the same temperature and ratio of HF to CH$_2$Cl$_2$ in Table 2 illustrates the superior results obtainable with low-ash content carbon. Comparison of the results in Table A with results using the same temperature and HF to CH$_2$Cl$_2$ in Table 1 illustrates superior results using low-ash content carbon containing even lesser amounts of trivalent chromium.

TABLE A

| Run Time (Hours) | Temp. °C. | Molar Ratio HF:CH$_2$Cl$_2$ | %32 | %31 | %30 |
|---|---|---|---|---|---|
| 19.0 | 200 | 2:1 | 0.2 | 2.9 | 96.9 |
| 43.0 | 260 | 2:1 | 20.5 | 12.3 | 67.2 |
| 45.0 | 275 | 2:1 | 25.6 | 12.6 | 61.8 |
| 46.0 | 275 | 4:1 | 37.0 | 13.4 | 49.6 |
| 49.0 | 250 | 4:1 | 13.0 | 13.6 | 73.5 |
| 50.0 | 225 | 4:1 | 1.2 | 6.2 | 92.6 |

Comparative Example B

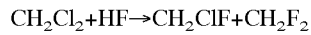
$CH_2Cl_2 + HF \rightarrow CH_2ClF + CH_2F_2$
Catalyst Preparation

A quartz tube was charged with 400 g of Carbon A. The carbon was washed with de-ionized water at a flow rate of 40 mL/min at room temperature for 72 hours. The carbon granules were then dried at 150° C. for 60 hours in air to obtain 373 g of dried granules. The ash content of this water washed carbon was about 1 weight percent.

A solution of CrCl$_3$.6H$_2$O (3.15 g) in de-ionized water (50 mL) was prepared in a round-bottomed flask. To this solution was added a portion (25.0 g) of the water washed carbon prepared as described above. The slurry was stirred on a rotary evaporator at room temperature at ambient pressure for 2 hours. The water was then removed under vacuum and the granules dried at 130° C. in nitrogen for 20 hours. The recovered catalyst weighed 26.65 g and contained about 7.5 weight percent CrCl$_3$.

Fluorination

The reactor was charged with a 7.5% CrCl$_3$ on water washed Carbon A (15 mL, 6.92 g) catalyst prepared as described above; and the catalyst was then activated according to the Activation Procedure above. The reaction temperature was varied from 200 to 300° C., the molar ratio of HF to CH$_2$Cl$_2$ was varied from 2:1 to 4:1 and the contact time was 15 seconds in all cases. The CH$_2$Cl$_2$ feed to the reactor contained 98.7% CH$_2$Cl$_2$ and 1.3% CH$_2$ClF. The reaction effluent was analyzed according to the Analytical Procedure above. The reaction results are shown in Table B. Comparison of the results in Table B with results in Table 1 and Table 2 illustrate the superior results obtainable using low-ash content carbon in accordance with this invention.

TABLE B

| Run Time (Hours) | Temp. °C. | Molar Ratio HF:CH2Cl2 | %32 | %31 | %30 |
|---|---|---|---|---|---|
| 5.0 | 250 | 2:1 | 33.7 | 13.2 | 53.1 |
| 18.0 | 200 | 4:1 | 3.4 | 11.0 | 85.6 |
| 37.0 | 225 | 2:1 | 28.6 | 12.4 | 58.9 |
| 52.0 | 225 | 4:1 | 35.5 | 13.6 | 50.7 |
| 66.0 | 250 | 4:1 | 56.0 | 13.7 | 30.1 |
| 73.0 | 300 | 4:1 | 53.6 | 15.7 | 30.4 |

Example 3

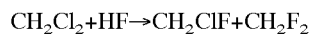
$CH_2Cl_2 + HF \rightarrow CH_2ClF + CH_2F_2$

The reactor was charged with a 10% CrCl$_3$ on HCl-washed Carbon B (15 mL, 6.5 g) catalyst and the catalyst was activated according to the Activation Procedure above.

The reaction temperature was varied from 200 to 250° C., the molar ratio of HF to $CH_2Cl_2$ was varied from 1:1 to 2:1 and the contact time was varied from 5 to 15 seconds. The $CH_2Cl_2$ feed to the reactor contained 98.9% $CH_2Cl_2$ and 1.1% $CH_2ClF$. The reaction effluent was analyzed according to the Analytical Procedure above. The reaction results are shown in Table 3.

TABLE 3

| Run Time (Hours) | Temp. ° C. | Molar Ratio HF:CH$_2$Cl$_2$ | C.T. Sec. | %32 | %31 | %30 |
|---|---|---|---|---|---|---|
| 4.0 | 200 | 2:1 | 15 | 8.4 | 11.2 | 80.5 |
| 7.0 | 225 | 2:1 | 15 | 25.7 | 10.7 | 63.6 |
| 26.0 | 215 | 2:1 | 15 | 27.0 | 10.5 | 62.4 |
| 31.0 | 210 | 2:1 | 15 | 23.5 | 10.8 | 65.7 |
| 33.0 | 205 | 2:1 | 15 | 13.3 | 10.5 | 76.2 |
| 35.5 | 225 | 1:1 | 5 | 13.6 | 9.1 | 77.3 |
| 38.0 | 225 | 2:1 | 5 | 25.1 | 11.0 | 63.9 |
| 39.5 | 250 | 2:1 | 5 | 27.2 | 11.8 | 61.1 |

Example 4

$$CH_2Cl_2 + HF \rightarrow CH_2ClF + CH_2F_2$$

The reactor was charged with a 20% $CrCl_3$ on HCl-washed Carbon B (15 mL, 6.6 g) catalyst and the catalyst was activated according to the Activation Procedure above. The reaction temperature was varied from 185 to 250° C., the molar ratio of HF to $CH_2Cl_2$ was varied from 1.5:1 to 2:1 and the contact time was varied from 5 to 15 seconds. The $CH_2Cl_2$ feed to the reactor contained 98.9% $CH_2Cl_2$ and 1.1% $CH_2ClF$. The reaction effluent was analyzed according to the Analytical Procedure above. The reaction results are shown in Table 4.

TABLE 4

| Run Time (Hours) | Temp. ° C. | Molar Ratio HF:CH$_2$Cl$_2$ | C.T. Sec. | %32 | %31 | %30 |
|---|---|---|---|---|---|---|
| 17.0 | 200 | 2:1 | 15 | 24.5 | 10.3 | 65.2 |
| 18.0 | 185 | 2:1 | 15 | 4.4 | 9.4 | 86.2 |
| 21.5 | 225 | 2:1 | 5 | 28.1 | 10.9 | 61.0 |
| 22.5 | 250 | 2:1 | 5 | 27.2 | 11.7 | 61.1 |
| 23.5 | 250 | 1.5:1 | 5 | 20.7 | 10.9 | 68.4 |

Example 5

$$CH_2Cl_2 + HF \rightarrow CH_2ClF + CH_2F_2$$

The reactor was charged with a 60% $CrCl_3$ on HCl-washed Carbon B (15 mL, 9.0 g) catalyst and the catalyst was activated according to the Activation Procedure above. The reaction temperature was varied from 150 to 200° C., the molar ratio of HF to $CH_2Cl_2$ was 2:1 and the contact time was 15 seconds. The $CH_2Cl_2$ feed to the reactor contained 98.9% $CH_2Cl_2$ and 1.1% $CH_2ClF$. The reaction effluent was analyzed according to the Analytical Procedure above. The reaction results are shown in Table 5.

TABLE 5

| Run Time (Hours) | Temp. ° C. | %32 | %31 | %30 |
|---|---|---|---|---|
| 17.0 | 200 | 29.2 | 9.9 | 60.8 |
| 20.5 | 150 | 4.2 | 9.7 | 86.1 |
| 22.5 | 160 | 13.3 | 11.1 | 75.6 |
| 24.0 | 165 | 18.6 | 9.5 | 71.9 |
| 25.0 | 170 | 22.2 | 8.5 | 69.3 |
| 34.5 | 175 | 17.8 | 10.4 | 71.8 |
| 101 | 175 | 20.1 | 9.8 | 70.1 |
| 133 | 175 | 26.7 | 8.8 | 64.5 |

Example 6

$$CH_2Cl_2(4) + CCl_3CF_3(1) + HF \rightarrow CH_2ClF + CH_2F_2 + CCl_2FCF_3$$

The reactor was charged with a 7.5% $CrCl_3$ on HCl-washed Carbon B (15 mL, 6.22 g) catalyst and the catalyst was activated according to the Activation Procedure above. The reaction temperature was varied from 275 to 350° C., and the contact time was varied from 5 to 15 seconds. The organic feed to the reactor consisted of 81.3 mole % $CH_2Cl_2$ and 18.2 mole % $CCl_3CF_3$ with the rest consisting essentially of 0.4 mole % $CHCl_2F$. The molar ratio of HF to the approximately 4:1 molar ratio mixture of $CH_2Cl_2$:$CCl_3CF_3$ was varied from 1.7:1 to 8:1. The reaction effluent was analyzed according to the Analytical Procedure above. The reaction results in mole % are shown in Table 6.

TABLE 6

| R.T. (Hrs) | T ° C. | Molar Ratio HF:(32 + 113a) | C.T. Sec. | %23 | %32 | %31 | %30 | %114a | %123 | %113a |
|---|---|---|---|---|---|---|---|---|---|---|
| 1.0 | 300 | 1.7:1 | 14 | 1.4 | 30.8 | 12.4 | 37.3 | 2.7 | 2.5 | 12.7 |
| 5.0 | 300 | 1.7:1 | 14 | 1.8 | 31.7 | 12.0 | 34.3 | 2.5 | 1.8 | 15.6 |
| 12.0 | 325 | 3.5:1 | 14 | 3.4 | 45.0 | 11.4 | 19.0 | 8.3 | 3.4 | 9.1 |
| 28.0 | 325 | 1.7:1 | 14 | 4.7 | 24.6 | 12.0 | 38.9 | 4.4 | 4.2 | 10.8 |
| 33.0 | 350 | 1.7:1 | 14 | 9.2 | 23.4 | 12.1 | 36.1 | 6.1 | 6.5 | 5.5 |
| 37.0 | 350 | 4:1 | 15 | 6.3 | 44.9 | 11.3 | 16.1 | 10.0 | 5.6 | 4.9 |
| 56.0 | 275 | 4:1 | 5 | 0.1 | 47.3 | 10.2 | 20.6 | 0.3 | 0.2 | 21.2 |
| 58.0 | 300 | 4:1 | 5 | 0.4 | 48.5 | 10.8 | 18.4 | 0.8 | 0.6 | 20.3 |
| 60.0 | 350 | 4:1 | 5 | 2.6 | 45.6 | 12.0 | 18.1 | 4.7 | 2.8 | 13.7 |
| 76.0 | 350 | 8:1 | 15 | 4.2 | 56.8 | 8.9 | 7.9 | 12.3 | 4.1 | 4.9 |
| 79.0 | 325 | 8:1 | 15 | 2.3 | 60.4 | 8.8 | 7.4 | 6.2 | 2.6 | 12.0 |

23 is $CHF_3$
114a is $CCl_2FCF_3$
123 is $CHCl_2CF_3$
113a is $CCl_3CF_3$

Example 7

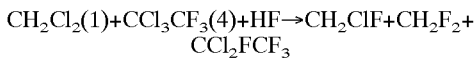
$$CH_2Cl_2(1) + CCl_3CF_3(4) + HF \rightarrow CH_2ClF + CH_2F_2 + CCl_2FCF_3$$

The reactor was charged with a 7.5% $CrCl_3$ on HCl-washed Carbon B (15 mL, 6.22 g) catalyst and the catalyst was activated according to the Activation Procedure above. The reaction temperature was 300° C., and the contact time was 18 seconds. The organic feed to the reactor consisted of 21.1 mole % $CH_2Cl_2$ and 78.1 mole % $CCl_3CF_3$ with the rest consisting essentially of 0.2 mole % $CHCl_2F$ and 0.4 mole % $CCl_2FCF_3$. The molar ratio of HF to the approximately 1:4 molar ratio mixture of $CH_2Cl_2$:$CCl_3CF_3$ was 4:1. The reaction effluent was analyzed according to the Analytical Procedure above. The reaction results in mole % are shown in Table 7.

TABLE 7

| R.T. (Hrs) | T ° C. | C.T. Sec | %23 | %32 | %31 | %30 | %114a | %123 | %113a |
|---|---|---|---|---|---|---|---|---|---|
| 2.0 | 300 | 18 | 0.2 | 13.8 | 1.4 | 1.0 | 7.3 | 0.7 | 75.4 |
| 19.0 | 300 | 18 | 0.1 | 13.2 | 1.3 | 0.8 | 7.3 | 0.4 | 76.6 |

What is claimed is:

1. A composition consisting essentially of hydrogen fluoride in combination with an effective amount of $CH_2ClF$ to form an azeotrope or azeotrope-like composition with hydrogen fluoride, said composition containing from about 58 to 65 mole percent $CH_2ClF$ and boiling at a temperature from about −25° C. to about 75° C.

2. The composition of claim 1 consisting essentially of an azeotropic combination of hydrogen fluoride with $CH_2ClF$, which contains from about 42 to about 35 mole percent HF and from about 58 to about 65 mole percent $CH_2ClF$.

3. The composition of claim 2 having a boiling point at about −25° C. and 55 kPa and containing about 42 mole percent HF and 58 mole percent $CH_2ClF$.

4. The composition of claim 2 having a boiling point at about 20° C. and 340 kPa and containing about 37.5 mole percent HF and 62.5 mole percent $CH_2ClF$.

5. The composition of claim 2 having a boiling point at about 75° C. and about 1700 kPa and containing about 35 mole percent HF and 65 mole percent $CH_2ClF$.

6. A composition consisting essentially of hydrogen fluoride in combination with an effective amount of $CH_2Cl_2$ to form an azeotrope or azeotrope-like composition with hydrogen fluoride, said composition comprising a two-phase liquid.

7. The composition of claim 6 having a boiling point at 20 C. and 143 kPa and containing about 85 mole percent HF and 15 mole percent $CH_2Cl_2$.

8. The composition of claim 6 having a boiling point at −50° C. and 5 kPa and containing about 95 mole percent HF and 5 mole percent $CH_2Cl_2$.

9. The composition of claim 6 wherein said two-phase liquid consists essentially of from about 95 to 71 mole percent HF and from about 5 to 29 mole percent $CH_2Cl_2$ and has a relative volatility of about 1.0.

10. A composition consisting essentially of hydrogen fluoride in combination with an effective amount of $CH_2Cl_2$ to form an azeotrope or azeotrope-like composition with hydrogen fluoride, said composition having a boiling point at 110° C. and about 2280 kPa and containing about 71 mole percent HF and 29 mole percent $CH_2Cl_2$.

11. The composition of claim 10 comprising a two-phase liquid.

* * * * *